United States Patent [19]
Rioux et al.

[11] 3,938,527
[45] Feb. 17, 1976

[54] INSTRUMENT FOR LAPAROSCOPIC TUBAL CAUTERIZATION

[75] Inventors: Jacques E. Rioux, Quebec; Gerald Turp, Dollard des Ormeaux; Francois Jacques, Mascouche, all of Canada

[73] Assignee: Centre de Recherche Industrielle de Quebec, Quebec, Canada

[22] Filed: July 13, 1973

[21] Appl. No.: 378,935

[30] Foreign Application Priority Data
July 4, 1973   Canada .................................. 175625

[52] U.S. Cl. ........................... 128/303.17; 128/321
[51] Int. Cl.² ..................................... A61B 17/36
[58] Field of Search ............ 128/321, 303.17, 354, 303.13, 128/303.14, 303.15

[56] References Cited
UNITED STATES PATENTS

| | | | |
|---|---|---|---|
| 1,731,069 | 10/1929 | Herman | 128/321 X |
| 1,813,902 | 7/1931 | Bovie | 128/303.14 |
| 1,908,201 | 5/1933 | Welch et al. | 128/303.17 |
| 2,033,397 | 3/1936 | Richman | 128/303.17 |
| 2,114,695 | 4/1938 | Anderson | 128/321 |
| 2,831,174 | 4/1958 | Hilmo | 128/321 UX |
| 3,451,395 | 6/1969 | Thyberg | 128/303.1 |
| 3,831,607 | 8/1974 | Lindemann | 128/303.17 |
| 3,858,586 | 1/1975 | Lessen | 128/303.17 X |

FOREIGN PATENTS OR APPLICATIONS

| | | | |
|---|---|---|---|
| 598,149 | 9/1925 | France | 128/303.17 |
| 200,355 | 7/1908 | Germany | 128/321 |
| 123,563 | 6/1931 | Austria | 128/321 |
| 1,378,088 | 8/1963 | France | 128/354 |

*Primary Examiner*—Channing L. Pace
*Attorney, Agent, or Firm*—Cushman, Darby & Cushman

[57] ABSTRACT

An instrument for laparoscopic tubal cauterization includes: a grip member, a probe element attached to the grip member and a pair of electrodes carried by the probe element in such spaced relationship to one another as to avoid electrical short therebetween, the electrodes defining at one extremity a pair of tube-grasping portions. Means are provided on the grip member for electrically connecting the electrodes to an external power source and for allowing a current discharge between the tube-grasping portions of the electrodes whereby the tube grasped is cauterized.

9 Claims, 7 Drawing Figures

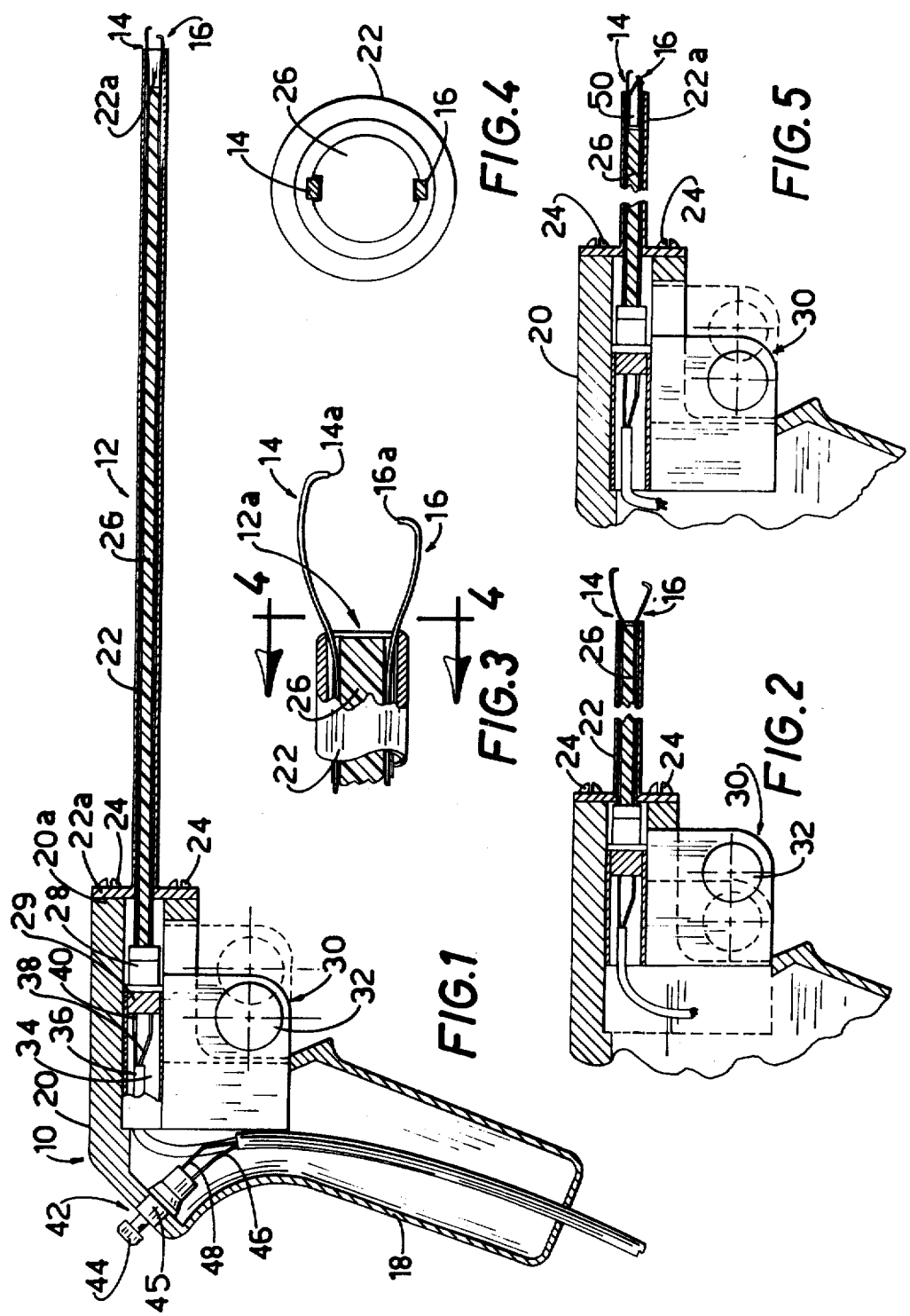

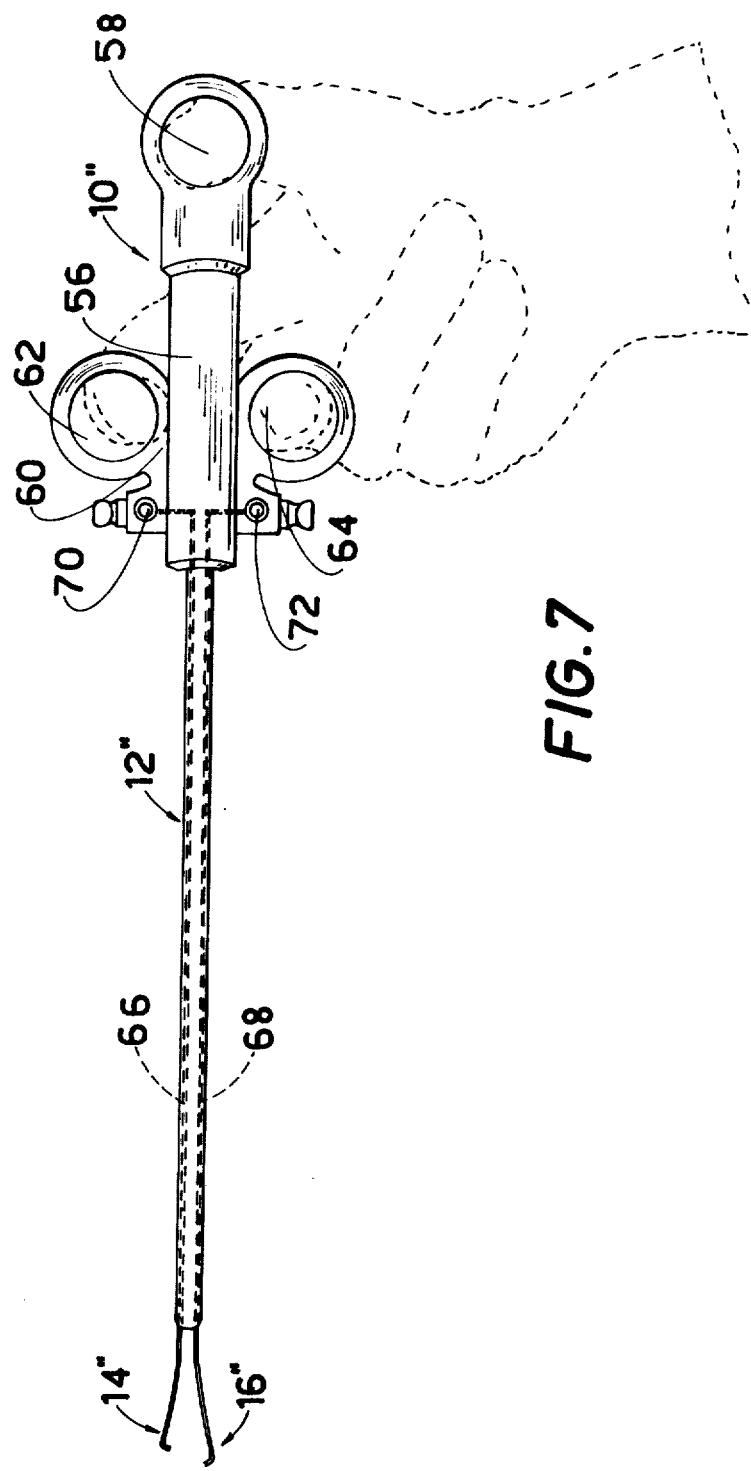

INSTRUMENT FOR LAPAROSCOPIC TUBAL CAUTERIZATION

FIELD OF THE INVENTION

This invention relates to an instrument for laparoscopic tubal cauterization.

Essentially, female sterilization involves cutting or blocking both fallopian tubes so that the egg released each month by the ovary cannot be reached and fertilized by the upwardly mobile sperm.

BACKGROUND OF THE INVENTION

Only recently, have new technologies emerged that promise to make female sterilization a short, outpatient procedure.

Laparoscopic sterilization already represents an outpatient procedure which may be done in some clinics and hospitals under local or general anaesthesia. Using specially designed instruments, including a laparoscope with fiber optic illumination, trained physicians can now see directly into the abdominal cavity and cut or block the fallopian tubes with only one or two small incisions.

Laparoscopic tubal cauterization consists basically in placing under the buttock and back of a patient a metal plate of fair dimensions which has been coated with a special conductive paste. This plate is electrically connected converting the whole body into one pole. An electro-surgical instrument, which has one extremity insertable in the abdominal cavity to contact a fallopian tube, represents the other pole. The gynecologist then causes a current discharge on the tube until it becomes completely blocked from coagulation.

The popularity of laparoscopic tubal cauterization is presently being tempered by a constant flow of reports on complications. Most of these complications are due to the fact that these electro-surgical instruments work on the principle of one electrode converting the body into one pole and the specific instrument being the other pole. Since the human body is a relatively poor electrical conductor, a huge input is needed to convert the body into one pole. As a result, it has been observed that there is quite a spillage of electricity by the instrument in the abdominal cavity thereby creating the danger of shock, cardiac arrest and even electrocution. The flow and direction of current is erratic and unpredictable and the very humid atmosphere inside the abdominal cavity and the serosity covering the organs increase the conductivity whereby production of intraabdominal sparking is made possible with secondary intestinal burning.

Outside the body, chemical burns resulting from the substance used for the preparation of the field between the skin and the plate have been found. Also, electrical burns from a malfunction of the unit and even actual fire burns with the use of a flammable material (alcohol) have occurred as a result of the production of a spark outside the body.

STATEMENT OF THE INVENTION

An object of this invention is the provision of an instrument which overcomes the above-noted disadvantages plaguing present electro-surgical instruments and which will enable such operations with a minimum of risk and inconvenience to the patient.

It is another object of the present invention to provide an instrument for laparoscopic tubal cauterization where the current discharge is greatly reduced. This is being achieved by providing an instrument where the two poles are used in a very localized area, that is directly on the grasped tube. Since the current passes directly through the tube from one terminal to the other, the coagulation is always under the control of the gynecologist.

The present invention therefore relates, in its broadest aspect, to an instrument which comprises: a grip member; a probe element having one end attached to the grip member; a pair of electrically conductive bipolar elements carried by the probe element in such spaced relationship to one another as to avoid electrical short therebetween, the bipolar elements having cooperating extremities defining tube-grasping portions; and means connecting each bipolar element to an external power source and for causing a current discharge between the tube-grasping portions whereby the tube grasped may be cauterized in its grasped area.

In one preferred form of the invention, the grip member is constructed in the form of a pistol with a finger actuatable slidable member mounted therein to effect the grasping and releasing movements of electrodes on the tube.

Yet, in another preferred form of the invention, the grip member is provided with a button so that the closing and interrupting of the circuit may be operated by the thumb of the gynecologist.

Another characteristic of the present invention is the provision of a detachable probe element. The disadvantage of presently used metallic probes is their cleaning and sterilization. The present invention provides a probe which may be easily assembled to a grip element and which may be disposed of after use.

The probe comprises an elongated sleeve member; a separator element slidably mounted in the sleeve member and made of an insulating material; a pair of electrodes mounted in spaced relationship to one another in the separator element, the electrodes having one end extending adjacent one open end of the sleeve member; and electrical connector means mounted to the opposite end of the separator element and receiving the opposite ends of the electrodes.

In a preferred form, the sleeve and separator element of the probe are made of a plastic material, such as nylon.

Other objects, purposes and characteristic features of the present invention will be, in part, obvious from the accompanying drawings and, in part, pointed out as the description of the invention progresses. In describing the invention in detail, reference will be made to the accompanying drawings, in which like reference characters designated corresponding parts throughout the several views and in which:

BRIEF DESCRIPTION OF THE DRAWINGS

FIG. 1 is a cross-sectional elevation view of a first embodiment of an instrument for laparoscopic tubal cauterization made in accordance with the present invention;

FIG. 2 is a cross-sectional elevation view showing, in part, the instrument illustrated in FIG. 1 with the electrodes in the opened position outside the probe element;

FIG. 3 is an enlarged view of one extremity of the probe element showing the electrodes in the opened position;

FIG. 4 is an end cross-sectional view taken along lines 4—4 of FIG. 3;

FIG. 5 is a cross-sectional elevation view illustrating, in part, a second embodiment of the present invention;

FIG. 7 is an elevation view of a fourth embodiment of the present invention.

Figure 6:
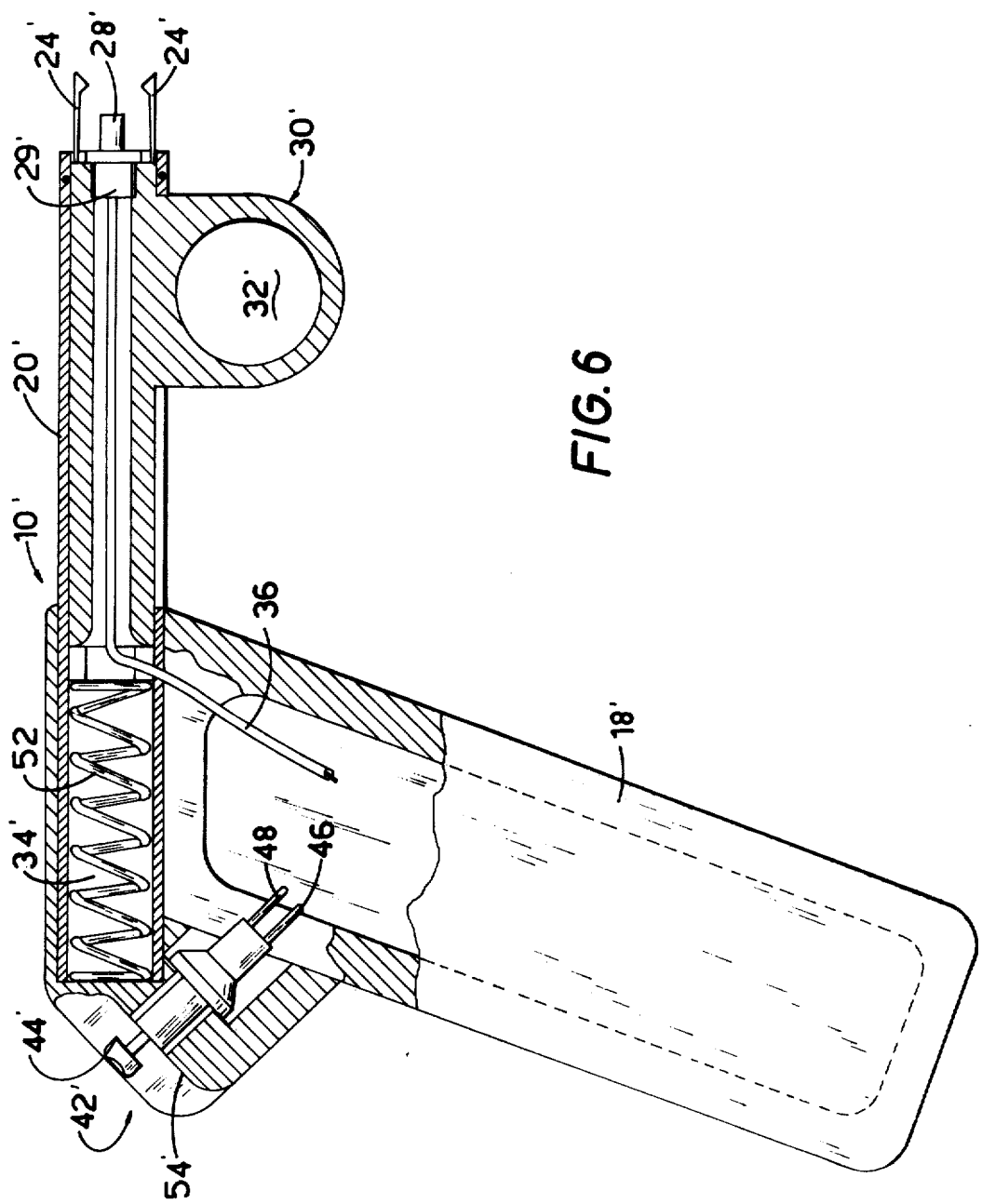
FIG. 6 is a partly cross-sectional elevation view of a third embodiment of the present invention.

Referring generally to the drawings, the instrument for use with laparoscopic tubal cauterization essentially comprises a grip member 10, a probe element 12 having one end attached to the grip member and a pair of electrically conductive bipolar elements or electrodes 14,16 which are carried by the probe element in a spaced relationship to one another. As it will be explained in greater detail hereinbelow, means are provided on the grip member 10 for electrically connecting the electrodes to an external power source and for generating a supply current to the electrodes.

DESCRIPTION OF FIRST EMBODIMENT

Referring now more particularly to the embodiment illustrated in FIGS. 1-4, the grip member 10 is shaped in the form of a pistol that includes a hand-gripping lower portion 18 and a probe-receiving upper portion 20, each portion defining a hollow housing.

The probe element 12 is shaped in the form of a tubular sleeve 22 with a flange 22a at one end thereof which is attached to a correspondingly-shaped extremity 20a of the grip portion 20 by appropriate fastening means 24. A separator element 26, made of a suitable insulating material, is slidably mounted inside sleeve 22. Diametrically spaced on the separator, a pair of flat metallic wires 14 and 16 extend inside the sleeve, preferably in parallel relationship to one another so as to avoid electrical short therebetween when current is supplied. A plug 28 is mounted to the end of the separator element 26 inside the housing of the upper portion 20 and is received in a socket 29 mounted in a recess 34 in the upper part of a slidable member 30. This member 30 has a fingerreceiving opening 32 at its lower part to permit actuation thereof in the longitudinal direction of the probe element. Electrical wires 38,40 of a cable 36 extending through housing 18 connect the socket 29 to an external power supply source (not shown). As illustrated in FIG. 2 in dotted lines, the slidable member 30 is longitudinally displaceable so that the outer ends 14a and 16a of the electrodes project outside the open end 22a of the sleeve 22.

Also mounted on the grip member 20 are switch means 42 consisting of a button 44 and its connection 45 with conductors 46,48 which are electrically connected through appropriate relay means (not shown) with the external power source so that, upon actuation of the button 44, energization of the power source causes a current supply to the electrodes.

Referring more particularly to FIGS. 2 and 3, actuation of the finger-operated slidable member 30 in the longitudinal direction of the probe element causes electrodes 14,16 to move out of sleeve 22. The material chosen for the electrodes should be sufficiently flexible so that, as they exit from the sleeve end, they open up and space from one another to appropriately receive the tube to be cauterized. The tube-grasping portions of the electrodes have inwardly bent extremities or tips 14a,16a, the planes of which are offset relative to one another so that, as the separator 26 is drawn in the sleeve 22 as a result of actuating member 30, the tips will not come in contact thereby avoiding a short circuit during the tube grasping operation.

In the embodiment illustrated in FIG. 5, the instrument is identical to that illustrated in FIGS. 1-4, except that a cutter 50 is fixedly mounted to the extremity 22a of the sleeve whereby as the electrodes are drawn in the sleeve with a tube grasped therebetween it is also possible to cut the cauterized tube.

OPERATION OF THE INSTRUMENT

The operation of the instrument will be best understood by describing the procedure followed during a laparoscopic tubal cauterization. The patient is given general anaesthesia; a small incision is made in the inferior fold of the umbilicus and a Verres cannula is then inserted into the peritoneal cavity for $CO_2$ insufflation. A sufficient quantity of $CO_2$ is insufflated while the patient is in a steep Trendelenburg position. A trocar is then introduced into the abdominal cavity and the laparoscope inserted through its sleeve.

A secondary stabbed wound is made in the mid-line or the right or left lower quadrant of the abdomen and the probe 12 is introduced under direct vision. Once received in the abdominal cavity, the electrodes are opened up by actuating the slidable member 30 to a position shown in FIG. 2. There, a tube is grasped and the slidable member is drawn in the housing further securing the grasping engagement of the electrodes on the tube. The gynecologist then actuates button 24 which causes the power source to allow a current discharge between the electrodes 14,16 cauterizing the area of the tube which is grasped. The button is released once the gynecologist considers, through his laparoscope, the tube to be sufficiently coagulated. The procedure is repeated three or four times along the tube to insure maximum cauterization. The same procedure is repeated on the other tube. Then, the instrument is retracted and sutures are placed in the skin.

Instead of using the above described two stabbed wound technique, the gynecologist may also use a sleeve of smaller and longer calibre which he introduces through a channel provided in the operating laparoscope. This technique does not alter the essential characteristics of the construction of the present invention.

DESCRIPTION OF OTHER EMBODIMENTS

FIG. 6 illustrates an instrument similar to the one described above but where the probe element has been omitted from the drawings for clarity purposes; however, in this embodiment a spring 52 is mounted in the upper housing of the grip member and has one end bearing against the housing of the grip member and the other end bearing against the slidable member 30'. The provision of such a spring facilitates the release of the electrodes from the cauterized tube and is especially advantageous since there is usually a tendency of the electrodes to stick to the cauterized tube.

Another feature of the embodiment illustrated in FIG. 6 consists in providing a cavity 54 in that portion of the grip member which serves to receive the switch means 42'. This cavity enables to conceal the button 44' thereby greatly reducing the chances of accidentally actuating the button.

Referring to FIG. 7, there is shown another embodiment of the present invention in schematic form but including all the essential elements. The grip member 10'' includes a first tubular member 56 one end of which has finger-receiving opening 58 and the sidewall of which includes a pair of opposite longitudinal slots (not shown) to receive therein a slidable member 60 provided with a pair of finger-receiving openings 62,64. The probe element 12″ is secured to member 56 while the electrodes 14″,16″ are electrically connected to and movable with member 60. Two male extensions 70,72 are provided on member 60 and are adapted to receive corresponding female sockets. In this case, the actuation of the power source may be carried out by a foot pedal near the gynecologist.

In another preferred form of the invention, it is preferable to coat the extremities 14a,16a of the electrodes with a non-sticking material, such as TEFLON, to prevent the electrodes from sticking on the cauterized tube. The grip member and probe element should be made of a plastic material thereby reducing the danger of shock.

Although the invention as been described above in relation to a plurality of specific forms, it will be evident to the man skilled in the art that it may be refined and modified in various ways. For example, the electrodes could have their extremities shaped in the form of a bird's beak so that, after cauterization, the tube could be cut by actuation of the electrodes. It is therefore wished to have it understood that the present invention is not limited to interpretation except by the terms of the following claims.

We claim:

1. Instrument for laparoscopic tubal cauterization by intra-abdominal cavity penetration comprising: a grip member; an elongated narrow probe element having one end removably attached to said grip member whereby said probe element may be disposed of after use; said probe element including a sleeve member; said sleeve member being shaped to be easily insertable through a small cut in the abdominal wall of said cavity and to reach a fallopian tube therein; a pair of electrically conductive bi-polar elements carried by said probe element within said sleeve member in such spaced relationship to one another as to avoid electrical short therebetween and longitudinally displaceable within said sleeve member; said elements having cooperating extremities defining tube-grasping portions; said extremities cooperating with the open end of said sleeve member for causing a strong squeezing action by said extremities externally on said tube being grasped; means on said grip member connecting each said member connecting each said bi-polar elements to an external power source and allowing a current discharge between the tube-grasping portions externally on the squeezed tube for complete coagulation of said tube.

2. An instrument as defined in claim 1 wherein said grip member includes a housing and a slidable member therein, said bipolar elements being connected to said slidable member whereby actuation of said slidable member in the longitudinal direction of the probe element results in the sliding displacement of said bipolar elements in said sleeve member.

3. An instrument as defined in claim 1 wherein said probe element include an insulating separator slidably mounted in said sleeve member; said bipolar elements being mounted to said separator, the cooperating extremities of said bipolar elements diverging outwardly outside the corresponding end of said sleeve member, said grip member including a housing and a slidable member mounted therein, said bipolar elements having their opposite extremities connected to said slidable member whereby actuation of said slidable member in the longitudinal direction of the probe element results in the sliding displacement of said bipolar elements in said sleeve member and in the contacting engagement of the outwardly diverging extremities of the elements with said corresponding end of said sleeve member whereby said tube-grasping portions of said elements are moved toward and away from each other.

4. An instrument as defined in claim 1 further comprising fastening means for attaching said probe element to said grip member whereby said probe element may be removed therefrom.

5. An instrument as defined in claim 2 further comprising spring means disposed in said housing of said grip member and acting on said slidable member for returning said slidable member after actuation thereof.

6. An instrument as defined in claim 2 wherein said means on said grip member include wire means mounted in said housing of said grip member connecting said bipolar elements to said power source and actuator means for causing said power source to pass current to said bipolar elements.

7. An instrument as defined in claim 6 wherein said grip member is pistol-shaped and includes a cavity in the outside wall to conceal said actuator means and to prevent accidental actuation thereof.

8. An instrument as defined in claim 1 wherein said tube-grasping portions are covered with a layer of antiadherent material.

9. An instrument as defined in claim 1 wherein said elements have inwardly bent portions, the planes of which are offset in relation to one another so as to avoid contact therebetween during a tube grasping operation.

* * * * *